(12) United States Patent
Bacus (10) Patent No.: US 8,623,604 B2
(45) Date of Patent: Jan. 7, 2014

(54) METHODS FOR PREDICTING RESPONSIVENESS OF A CANCER CELL TO AN ANTI-IGFR1 ANTIBODY BY ANALYSIS OF MUTATIONS IN PIK3CA

(75) Inventor: Sarah Bacus, Hinsdale, IL (US)

(73) Assignee: Quintiles Transnational Corp., Durham, NC (US)

( * ) Notice: Subject to any disclaimer, the term of this patent is extended or adjusted under 35 U.S.C. 154(b) by 297 days.

(21) Appl. No.: 12/878,156

(22) Filed: Sep. 9, 2010

(65) Prior Publication Data

US 2011/0060605 A1  Mar. 10, 2011

Related U.S. Application Data

(60) Provisional application No. 61/240,782, filed on Sep. 9, 2009.

(51) Int. Cl.
*C12Q 1/68* (2006.01)

(52) U.S. Cl.
USPC .......................................... 435/6.14; 435/6.11

(58) Field of Classification Search
None
See application file for complete search history.

(56) References Cited

U.S. PATENT DOCUMENTS

| | | | |
|---|---|---|---|
| 6,248,527 B1 | 6/2001 | Chen et al. | |
| 6,498,012 B2 | 12/2002 | Laken | |
| 7,863,437 B2 * | 1/2011 | Hedtjarn | 536/24.5 |
| 8,137,919 B2 * | 3/2012 | Mariadason et al. | 435/6.14 |
| 2007/0048754 A1 | 3/2007 | Freeman et al. | |
| 2007/0099847 A1 | 5/2007 | Goldfine et al. | |
| 2009/0203718 A1 | 8/2009 | Rusnak et al. | |

OTHER PUBLICATIONS

Rexer et al., Exon 9 and exon 20 mutations in PIK3CA confer resistance to HER2 inhibitors in HER2-overexpressing breast cancer cells. Cancer Res. 69, (Suppl.1), Abstract#4054, 2009.*
Berns et al., A Functional Genetic Approach Identifies the PI3K Pathway as a Major Determinant of Trastuzumab Resistance in Breast Cancer. Cancer Cell, 12, 395-402, 2007.*
Eichhorn et al., Phosphatidylinositol 3-Kinase Hyperactivation Results in Lapatinib Resistance that is Reversed by the mTOR/Phosphatidylinositol 3-Kinase Inhibitor NVPBEZ235. Cancer Res., 68, 9221-9230, 2008.*
Kolasa et al. PIK3CA amplification associates with resistance to chemotherapy in ovarian cancer patients. Cancer Biol. & Therapy, 8, 21-26, 2009.*
Samuels et al., Oncogenic PI3K and its role in cancer. Curr. Opin. Oncol. 18, 77-82, 2006.*
Samuels et al., High Frequency of Mutations of the PIK3CA Gene in Human Cancers. Science, 304, 554, 2004.*
Vasudevan et al., AKT Independent Signaling Downstream of Oncogenic PIK3CA Mutations in Human Cancer. Cancer Cell, 16, 21-32, 2009.*
Belaus et al., Crosstalk between the extracellular domain of the ErbB2 receptor and IGF-1 receptor signaling, J. Ster. Biochem. Mol. Biol., 85, 105-115, 2003.*
Kataoka et al. Association between gain-of-function mutations in PIK3CA and resistance to HER2-targeted agents in HER2-amplified breast cancer cell lines, Annals of Oncology, Feb. 2010 (published online Jul. 24, 2009), pp. 1-8; abstract, vol. 21(2), 255-62, 2010.
International Search Report and Written Opinion for International Application No. PCT/US2010/048275, dated Nov. 15, 2010.

* cited by examiner

*Primary Examiner* — Elly-Gerald Stoica
(74) *Attorney, Agent, or Firm* — K&L Gates LLP (57) ABSTRACT

The present disclosure relates generally to methods and materials for determining the responsiveness of a subject with a disease or disorder to an inhibitor of a receptor tyrosine kinase including, for example, IGF1R. Such methods may comprise obtaining a biological sample from the subject, assaying the biological sample for one or more PIK3CA mutations, determining if one or more PIK3CA mutations are present in the biological sample, and employing the determination of one or more PIK3CA mutations in the biological sample to predict responsiveness of the subject to the receptor tyrosine kinase inhibitor.

26 Claims, 2 Drawing Sheets

Figure 2

METHODS FOR PREDICTING RESPONSIVENESS OF A CANCER CELL TO AN ANTI-IGFR1 ANTIBODY BY ANALYSIS OF MUTATIONS IN PIK3CA

BACKGROUND

The epidermal growth factor receptor (EGFR) family comprises four closely related receptors including, for example, HER1/EGFR, HER2, HER3 and HER4 ("HER family members") that are involved in cellular responses such as differentiation and proliferation. HER family members are typically involved in stimulating signaling pathways (e.g., PI3K signaling pathway) that promote multiple processes that are potentially cancer-promoting (e.g. proliferation, angiogenesis, cell motility and invasion, decreased apoptosis and induction of drug resistance). As such, over-expression of Her family members are frequently associated with many cancers including, for example, breast, lung, colorectal, ovarian, renal cell, bladder, head and neck cancers, glioblastomas, and astrocytomas.

Several Her family antagonists have been shown to offer clinical benefit for the treatment of cancer including, for example, erlotinib, gefitinib and lapatinib. Anti-EGFR antibodies have also shown clinical utility, including cetuximab and panitumamab which are approved for the treatment of EGFR-expressing, metastatic colorectal carcinoma. A breakthrough in the field of EGFR-targeted therapy occurred in 2004 with the identification of somatic mutations in the EGFR gene, which were closely associated with a favorable clinical response to gefitinib and erlotinib treatment in NSCLC patients. These genetic alterations consisted of small in-frame deletions or point mutations in EGFR exons 18-24, which encode the kinase domain of the protein and are clustered in two mutational 'hot spots' in the EGFR gene.

In addition to the EGFR family, the type 1 IGF receptor (IGF1R) has recently become a recognized target for the treatment of cancer. IGF1R is a transmembrane receptor tyrosine kinase (RTK) that is responsible for mediating IGF bioactivity. The IGF1R gene is located on chromosome 15q26 and encodes a single polypeptide of 1367 amino acids that is constitutively expressed in most cells. IGF1R is frequently overexpressed in tumours, including melanomas, cancers of the colon, pancreas, prostate and kidney. IGF1R activation may lead to autophosphorylation on tyrosines 1131, 1135 and 1136 in the kinase domain, followed by phosphorylation of juxtamembrane tyrosines and carboxy-terminal serines. IGF1R activation or overexpression is associated with an increased propensity for tumor cell invasion and metastasis. IGF1R activation also protects cells from a variety of apoptosis-inducing agents, including osmotic stress, hypoxia and anti-cancer drugs. IGF1R is also believed to suppress apoptosis primarily through the phosphoinositide 3-kinase (PI3K) pathway. Following phosphorylation of IRS-1 by the activated IGF1R, PI3K is activated by binding its regulatory subunit to IRS-1. This interaction leads to an increase in the levels of phosphatidylinositol 3,4,5-triphosphate ($PIP_3$), which leads to recruitment and activation of phosphoinositide-dependent kinase-1 and AKT/protein kinase B. Given that IGF1R is an important target for cancer therapy, methods are needed to determine whether a subject will be responsive to treatment with an IGF1R inhibitor.

SUMMARY

The present disclosure provides methods and materials for predicting the responsiveness of a disease or disorder to a receptor tyrosine kinase inhibitor, such as an IGF1R inhibitor, by analysis of one or more mutations in phosphatidylinositol 3-kinase, catalytic, alpha polypeptide (PIK3CA) (SEQ ID NO 1).

The present disclosure provides methods for predicting responsiveness of a cell to a receptor tyrosine kinase inhibitor by obtaining a cell; assaying the cell for one or more PIK3CA mutations; determining if one or more PIK3CA mutations are present in the cell; and employing the determination of one or more PIK3CA mutations in the cell to predict responsiveness of the cell to the receptor tyrosine kinase inhibitor (e.g., an IGF1R inhibitor).

The present disclosure also provides methods for predicting responsiveness of a subject with a disease or disorder to a receptor tyrosine kinase inhibitor (e.g., an IGF1R inhibitor) by obtaining a biological sample from the subject; assaying the biological sample for one or more PIK3CA mutations; determining if one or more PIK3CA mutations are present in the biological sample; and employing the determination of one or more PIK3CA mutations in the biological sample to predict responsiveness of the subject to the receptor tyrosine kinase inhibitor.

The present disclosure also provides methods for treating a subject with a disease or disorder by obtaining a biological sample from the subject by assaying the biological sample for one or more PIK3CA mutations, determining if one or more PIK3CA mutations are present in the biological sample; and administering to the subject a therapeutically effective amount of one or more receptor tyrosine kinase inhibitors where one or more PIK3CA mutations are present in the biological sample obtained from the subject.

The present disclosure also provides methods for doing business by selecting subjects for a clinical trial that are responsive to a receptor tyrosine kinase inhibitor by obtaining a biological sample from the subjects; assaying the biological samples obtained from the subjects for one or more PIK3CA mutations; determining if one or more PIK3CA mutations are present in the biological sample; selecting subjects for inclusion in a clinical trial that are responsive to the tyrosine kinase inhibitor; and seeking regulatory approval for the drug.

In an embodiment of any of the above-described methods, the cell expresses IGF1R.

In an embodiment of any of the above-described methods, the receptor tyrosine kinase inhibitor is an IGF1R inhibitor.

In an embodiment of any of the above-described methods, PIK3CA has the amino acid sequence set forth in SEQ ID NO: 1.

In an embodiment of any of the above-described methods, the one or more mutations in PIK3CA are selected from the group consisting of: E542K, E545K, E545G, E545D, Q546K, Q546R, M1043I, M1043V, H1047R, H1047L, H1047Y, G1049R and G1049S.

In an embodiment of any of the above-described methods, the presence one or more PIK3CA mutations in the cell predicts that the cell will be responsive to the receptor tyrosine kinase inhibitor.

In an embodiment of any of the above-described methods, the cell is assayed for PIK3CA mutations by analyzing nucleic acid obtained from the cell. In an embodiment of any of the above-described methods, the cell is assayed for PIK3CA mutations by analyzing proteins obtained from the cell.

In an embodiment of any of the above-described methods, the receptor tyrosine kinase inhibitor is an antibody. In an embodiment of any of the above-described methods, the antibody is a monoclonal antibody. In an embodiment of any of the above-described methods, the receptor tyrosine kinase inhibitor is a small molecule.

In an embodiment of any of the above-described methods, the cell is from a tumor biopsy. In an embodiment of any of the above-described methods, the cell is from an aspirate. In an embodiment of any of the above-described methods, the cell is from a cancer patient.

In an embodiment of any of the above-described methods, the biological sample expresses IGF1R.

In an embodiment of any of the above-described methods, the presence one or more PIK3CA mutations in the biological sample predicts that the subject will be responsive to the receptor tyrosine kinase inhibitor (e.g., an IGF1R inhibitor).

In an embodiment of any of the above-described methods, the biological sample is assayed for PIK3CA mutations by analyzing nucleic acid obtained from the sample. In an embodiment of any of the above-described methods, the biological sample is assayed for PIK3CA mutations by analyzing proteins obtained from the sample.

In an embodiment of any of the above-described methods, the disease or disorder is cancer. In an embodiment of any of the above-described methods, the cancer is selected from the group consisting of gastrointestinal cancer, prostate cancer, ovarian cancer, breast cancer, head and neck cancer, lung cancer, non-small cell lung cancer, cancer of the nervous system, kidney cancer, retina cancer, skin cancer, liver cancer, pancreatic cancer, genital-urinary cancer and bladder cancer.

In an embodiment of any of the above-described methods, the biological sample is a tumor biopsy.

In an embodiment of any of the above-described methods, the biological sample is an aspirate. In an embodiment of any of the above-described methods, the subject is a cancer patient.

In an embodiment of any of the above-described methods, the therapeutically effective amount of one or more tyrosine kinase inhibitors are optionally adapted for a co-treatment with radiotherapy or radio-immunotherapy.

In an embodiment of any of the above-described methods, the clinical trial is a phase II, III or IV clinical trial.

In an embodiment of any of the above-described methods, the IGF1R inhibitor is a tyrphostin such as AG538 or AG1024. In an embodiment of any of the above-described methods, the IGF1R inhibitor is a pyrrolo(2,3-d)-pyrimidine derivative such as NVP-AEW541. In an embodiment of any of the above-described methods, the IGF1R inhibitor is a monoclonal antibody (e.g., figitumab).

BRIEF DESCRIPTION OF THE DRAWINGS

The foregoing summary, as well as the following detailed description of the disclosure, will be better understood when read in conjunction with the appended figures. For the purpose of illustrating the disclosure, shown in the figures are embodiments which are presently preferred. It should be understood, however, that the disclosure is not limited to the precise arrangements, examples and instrumentalities shown.

DETAILED DESCRIPTION

Receptor tyrosine kinase inhibitors are often used in the treatment of diseases and/or disorders such as cancer. However, some subjects respond to treatment with a receptor tyrosine kinase inhibitor while other subject do not respond to such treatment. Thus, biomarkers and methods are needed which can be used to predict whether a particular subject will be responsive to treatment with a receptor tyrosine kinase inhibitor including, for example, an IGF1R inhibitor, or whether the subject will not be responsive to treatment with the receptor tyrosine kinase inhibitor including, for example, an IGF1R inhibitor. Notably, the inventor of the instant application has unexpectedly found that mutations in PIK3CA correlate with responsiveness to a receptor tyrosine kinase inhibitor such as an IGF1R inhibitor. Interestingly, cells that harbor mutations in PIK3CA have been shown to respond to treatment with an IGF1R inhibitor (e.g., an antibody to IGF1R) while cells that are wild-type for PIK3CA have been shown not respond to treatment with an IGF1R inhibitor (e.g., an antibody to IGF1R). Accordingly, the methods of the instant application may be used to successfully predict whether a subject will be responsive to treatment with a receptor tyrosine kinase inhibitor (e.g., an IGF1R inhibitor such as an IGF1R antibody or small molecule).

The present disclosure provides methods for predicting responsiveness of a cell to a receptor tyrosine kinase inhibitor (e.g., an IGF1R inhibitor) by obtaining a cell; assaying the cell for one or more PIK3CA mutations; determining if one or more PIK3CA mutations are present in the cell; and employing the determination of one or more PIK3CA mutations in the cell to predict responsiveness of the cell to the receptor tyrosine kinase inhibitor. The one or more mutations in PIK3CA may be selected from the group consisting of: E542K, E545K, E545G, E545D, Q546K, Q546R, M1043I, M1043V, H1047R, H1047L, H1047Y, G1049R and G1049S. The presence of one or more mutations in PIK3CA in the cell may predict that the subject will be responsive to treatment with an IGF1R inhibitor.

The present disclosure provides method for predicting responsiveness of a subject with a disease or disorder to a receptor tyrosine kinase inhibitor (e.g., an IGF1R inhibitor) by obtaining a biological sample from the subject; assaying the biological sample for one or more PIK3CA mutations (e.g., using IHC); determining if one or more PIK3CA mutations are present in the biological sample; and employing the determination of one or more PIK3CA mutations in the biological sample to predict responsiveness of the subject to the receptor tyrosine kinase inhibitor. The one or more mutations in PIK3CA may be selected from the group consisting of: E542K, E545K, E545G, E545D, Q546K, Q546R, M1043I, M1043V, H1047R, H1047L, H1047Y, G1049R and G1049S. The presence of one or more mutations in PIK3CA in the biological sample may predict that the subject will be responsive to treatment with an IGF1R inhibitor.

The present disclosure also provides methods for treating a subject with a disease or disorder by obtaining a biological sample from the subject, assaying the biological sample for one or more PIK3CA mutations, determining if one or more PIK3CA mutations are present in the biological sample; and administering to the subject a therapeutically effective amount of one or more receptor tyrosine kinase inhibitors (e.g., IGF-1R) where one or more PIK3CA mutations are present in the biological sample from the subject. The one or more mutations in PIK3CA may be selected from the group consisting of: E542K, E545K, E545G, E545D, Q546K, Q546R, M1043I, M1043V, H1047R, H1047L, H1047Y, G1049R and G1049S. The presence of one or more mutations in PIK3CA in the biological sample may predict that the subject will be responsive to treatment with an IGF1R inhibitor.

The present disclosure also provides methods for doing business by selecting subjects for a clinical trial that are responsive to a receptor tyrosine kinase inhibitor (e.g., IGF-1R) by obtaining a biological sample from the subjects; assaying the biological samples obtained from the subjects for one or more PIK3CA mutations; determining if one or more PIK3CA mutations are present in the biological sample; selecting subjects for inclusion in a clinical trial that are responsive to the tyrosine kinase inhibitor (e.g., those subjects in which their biological samples indicates the presence of one or more mutations in PIK3CA); and seeking regulatory approval for the drug. The one or more mutations in PIK3CA may be selected from the group consisting of: E542K, E545K, E545G, E545D, Q546K, Q546R, M1043I, M1043V, H1047R, H1047L, H1047Y, G1049R and G1049S. The presence of one or more mutations in PIK3CA in the biological sample may predict that the subject will be responsive to treatment with an IGF1R inhibitor.

PIK3CA may comprise the amino acid sequence as set forth in SEQ ID NO: 1. Alternatively, PIK3CA may be a variant including, for example, a biologically active variant, of the amino acid sequence as set forth in SEQ ID NO: 1. IGF1R may comprise the amino acid sequence as set forth in SEQ ID NO: 2. Alternatively, IGF1R may be a variant including, for example, a biologically active variant, of the amino acid sequence as set forth in SEQ ID NO: 2.

Guidance in determining which amino acid residues can be substituted, inserted, or deleted without abolishing biological or immunological activity can be found using computer programs well known in the art, such as DNASTAR software. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

Mutations in PIK3CA are mostly missense mutations; no truncating or nonsense mutations have been identified, but a few cases of in-frame deletions and insertions have been detected.

Protein variants include glycosylated forms, aggregative conjugates with other molecules, and covalent conjugates with unrelated chemical moieties. Also, protein variants also include allelic variants, species variants, and muteins. Truncations or deletions of regions which do not affect the differential expression of the gene are also variants. Covalent variants can be prepared by linking functionalities to groups which are found in the amino acid chain or at the N- or C-terminal residue, as is known in the art.

It will be recognized in the art that some amino acid sequence of PIK3CA can be varied without significant effect on the structure or function of the protein. If such differences in sequence are contemplated, it should be remembered that there are critical areas on the protein which determine activity. In general, it is possible to replace residues that form the tertiary structure, provided that residues performing a similar function are used. In other instances, the type of residue may be completely unimportant if the alteration occurs at a non-critical region of the protein. The replacement of amino acids can also change the selectivity of binding to cell surface receptors. Thus, the polypeptides of the present invention may include one or more amino acid substitutions, deletions or additions, either from natural mutations or human manipulation.

Amino acids in the polypeptides of the present invention that are essential for function can be identified by methods known in the art, such as site-directed mutagenesis or alanine-scanning mutagenesis (Cunningham and Wells, *Science* 244: 1081-1085 (1989)). The latter procedure introduces single alanine mutations at every residue in the molecule. The resulting mutant molecules are then tested for biological activity such as binding to a natural or synthetic binding partner. Sites that are critical for ligand-receptor binding can also be determined by structural analysis such as crystallization, nuclear magnetic resonance or photoaffinity labeling (Smith, et al., *J. Mol. Biol.* 224:899-904 (1992) and de Vos, et al. *Science* 255:306-312 (1992)).

Variants of PIK3CA may include a protein possessing an amino acid sequence that possess at least 90% sequence identity, more preferably at least 91% sequence identity, even more preferably at least 92% sequence identity, still more preferably at least 93% sequence identity, still more preferably at least 94% sequence identity, even more preferably at least 95% sequence identity, still more preferably at least 96% sequence identity, even more preferably at least 97% sequence identity, still more preferably at least 98% sequence identity, and most preferably at least 99% sequence identity, to PIK3CA (SEQ ID NO: 1). Preferably, this variant may possess at least one biological property in common with the native protein.

Sequence identity or percent identity is intended to mean the percentage of the same residues shared between two sequences, when the two sequences are aligned using the Clustal method [Higgins et al, Cabios 8:189-191 (1992)] of multiple sequence alignment in the Lasergene biocomputing software (DNASTAR, INC, Madison, Wis.). In this method, multiple alignments are carried out in a progressive manner, in which larger and larger alignment groups are assembled using similarity scores calculated from a series of pairwise alignments. Optimal sequence alignments are obtained by finding the maximum alignment score, which is the average of all scores between the separate residues in the alignment, determined from a residue weight table representing the probability of a given amino acid change occurring in two related proteins over a given evolutionary interval. Penalties for opening and lengthening gaps in the alignment contribute to the score. The default parameters used with this program are as follows: gap penalty for multiple alignment=10; gap length penalty for multiple alignment=10; k-tuple value in pairwise alignment=1; gap penalty in pairwise alignment=3; window value in pairwise alignment=5; diagonals saved in pairwise alignment=5. The residue weight table used for the alignment program is PAM250 [Dayhoff, et al., in Atlas of Protein Sequence and Structure, Dayhoff, Ed., NDRF, Washington, Vol. 5, suppl. 3, p. 345, (1978)].

In one embodiment, the disease or disorder may be cancer. In one embodiment the cancer may be selected from the group consisting of: oral cancer, prostate cancer, rectal cancer, non-small cell lung cancer, lip and oral cavity cancer, liver cancer, lung cancer, anal cancer, kidney cancer, vulvar cancer, breast cancer, oropharyngeal cancer, nasal cavity and paranasal sinus cancer, nasopharyngeal cancer, urethra cancer, small intestine cancer, bile duct cancer, bladder cancer, ovarian cancer, laryngeal cancer, hypopharyngeal cancer, gallbladder cancer, colon cancer, colorectal cancer, head and neck cancer, glioma; parathyroid cancer, penile cancer, vaginal cancer, thyroid cancer, pancreatic cancer, esophageal cancer, Hodgkin's lymphoma, leukemia-related disorders, mycosis fungoides, and myelodysplastic syndrome.

In another embodiment the cancer may be non-small cell lung cancer, pancreatic cancer, breast cancer, ovarian cancer, colorectal cancer, or head and neck cancer. In yet another embodiment the cancer may be a carcinoma, a tumor, a neoplasm, a lymphoma, a melanoma, a glioma, a sarcoma, or a blastoma.

In one embodiment the carcinoma may be selected from the group consisting of: carcinoma, adenocarcinoma, adenoid cystic carcinoma, adenosquamous carcinoma, adrenocortical carcinoma, well differentiated carcinoma, squamous cell carcinoma, serous carcinoma, small cell carcinoma, invasive squamous cell carcinoma, large cell carcinoma, islet cell carcinoma, oat cell carcinoma, squamous carcinoma, undifferentiatied carcinoma, verrucous carcinoma, renal cell carcinoma, papillary serous adenocarcinoma, merkel cell carcinoma, hepatocellular carcinoma, soft tissue carcinomas, bronchial gland carcinomas, capillary carcinoma, bartholin gland carcinoma, basal cell carcinoma, carcinosarcoma, papilloma/carcinoma, clear cell carcinoma, endometrioid adenocarcinoma, mesothelial, metastatic carcinoma, mucoepidermoid carcinoma, cholangiocarcinoma, actinic keratoses, cystadenoma, and hepatic adenomatosis.

In another embodiment the tumor may be selected from the group consisting of: astrocytic tumors, malignant mesothelial tumors, ovarian germ cell tumors, supratentorial primitive neuroectodermal tumors, Wilms tumors, pituitary tumors, extragonadal germ cell tumors, gastrinoma, germ cell tumors, gestational trophoblastic tumors, brain tumors, pineal and supratentorial primitive neuroectodermal tumors, pituitary tumors, somatostatin-secreting tumors, endodermal sinus tumors, carcinoids, central cerebral astrocytoma, glucagonoma, hepatic adenoma, insulinoma, medulloepithelioma, plasmacytoma, vipoma, and pheochromocytoma.

In yet another embodiment the neoplasm may be selected from the group consisting of: intraepithelial neoplasia, multiple myeloma/plasma cell neoplasm, plasma cell neoplasm, interepithelial squamous cell neoplasia, endometrial hyperplasia, focal nodular hyperplasia, hemangioendothelioma, and malignant thymoma. In a further embodiment the lymphoma may be selected from the group consisting of: nervous system lymphoma, AIDS-related lymphoma, cutaneous T-cell lymphoma, non-Hodgkin's lymphoma, lymphoma, and Waldenstrom's macroglobulinemia. In another embodiment the melanoma may be selected from the group consisting of: acral lentiginous melanoma, superficial spreading melanoma, uveal melanoma, lentigo maligna melanomas, melanoma, intraocular melanoma, adenocarcinoma nodular melanoma, and hemangioma. In yet another embodiment the sarcoma may be selected from the group consisting of: adenomas, adenosarcoma, chondosarcoma, endometrial stromal sarcoma, Ewing's sarcoma, Kaposi's sarcoma, leiomyosarcoma, rhabdomyosarcoma, sarcoma, uterine sarcoma, osteosarcoma, and pseudosarcoma. In one embodiment the glioma may be selected from the group consisting of: glioma, brain stem glioma, and hypothalamic and visual pathway glioma. In another embodiment the blastoma may be selected from the group consisting of: pulmonary blastoma, pleuropulmonary blastoma, retinoblastoma, neuroblastoma, medulloblastoma, glioblastoma, and hemangiblastomas.

Detection and Quantitation of PIK3CA

A number of methodologies may be employed to detect and/or quantitate the amount (i.e., level) of mutant PIK3CA expression in a biological sample. Such expression of mutant PIK3CA (e.g., the one or more mutations in PIK3CA are selected from the group consisting of: E542K, E545K, E545G, E545D, Q546K, Q546R, M1043I, M1043V, H1047R, H1047L, H1047Y, G1049R and G1049S) may be detected at the protein level and/or nucleic acid level. Those skilled in the art will appreciate that the methods indicated below represent some of the preferred ways in which the level of PIK3CA expression may be detected and/or quantitated and in no manner limit the scope of methodologies that may be employed. Those skilled in the art will also be able to determine operative and optimal assay conditions for each determination by employing routine experimentation. Such methods may include but are not limited to Western blots, ELISA, immunoprecipitation, immunofluorescence, flow cytometry, northern blots, PCR and immunocytochemistry (IHC). In a preferred embodiment, expression of PIK3CA including, mutated PIK3CA (e.g., the one or more mutations in PIK3CA are selected from the group consisting of: E542K, E545K, E545G, E545D, Q546K, Q546R, M1043I, M1043V, H1047R, H1047L, H1047Y, G1049R and G1049S) may be detected and quantitated by IHC. Such methods of the present disclosure may comprise the detection and quantitation of the amount of the PIK3CA in a biological sample. PIK3CA may comprise the amino acid sequence as set forth in SEQ ID NO: 1. Alternatively, PIK3CA may be a variant of the amino acid sequence as set forth in SEQ ID NO: 1 and defined herein.

Biological samples that may be used in the methods of the present disclosure may include tissues, cells, biological fluids and isolates thereof, isolated from a subject, as well as tissues, cells and fluids present within a subject (e.g., a patient). Preferably, biological samples comprise cells, most preferably tumor cells, that are isolated from body samples, such as, but not limited to, smears, sputum, biopsies, secretions, cerebrospinal fluid, bile, blood, lymph fluid, urine and faeces, or tissue which has been removed from organs, such as breast, lung, intestine, skin, cervix, prostate, and stomach. Biological samples may also include sections of tissues such as frozen sections taken for histological purposes.

Immunohistochemistry (IHC) Assays

The expression level of mutant PIK3CA in a biological sample may be determined by immunohistochemically staining cells in the sample using a detectably-labeled agent (e.g., an antibody) specific for mutant PIK3CA. In a preferred embodiment, the agent is a monoclonal antibody and the detectable label is a chromagen or a fluorophore.

Mutant PIK3CA can be detected using a specific agent, most preferably an antibody, that is itself detectably labeled, or using an unlabeled antibody specific for mutant PIK3CA and a second antibody that is detectably labeled and recognizes the unlabeled antibody specific for mutant PIK3CA. Alternatively, any molecule that can be detectably labeled and that specifically binds to mutant PIK3CA can be used in the practice of the methods of the disclosure. In a preferred embodiment of the methods of the present disclosure, a two-component immunohistochemical staining system may be used to differentially stain mutant PIK3CA and the tissue or cell sample so that the stained mutant PIK3CA can be more readily distinguished from the counterstained tissue or cell sample.

In an exemplary method, mutant PIK3CA in the biological sample may be identified by adding a detectably-labeled primary antibody specific for mutant PIK3CA, or alternatively an unlabeled primary antibody and a detectably-labeled secondary antibody specific for the primary antibody. The antibodies are incubated with the sample for a time to form complexes if mutant PIK3CA is present.

The complexes may then visualized by treating the sections with a stain such as diaminobenzidine (DAB) stain under appropriate conditions. In a second step, the tissue may be counterstained with another optical enhancement factor, for example ethyl green. Although a staining technique using peroxidase and ethyl green is exemplary, other stains and optical enhancement factors are also suitable such as alkaline phosphatase based with specific chromagens such as Fast Red, Fast Green, etc. For example, PIK3CA can be stained using diaminobenzidine (DAB) and the tissue or cell sample can be counterstained using ethyl green or methylene blue. Spectral studies have shown that the ethyl green stain offers good spectral separation from the DAB precipitate of the immunoperoxidase technique such that different features of the image can be readily separated by filtering it at two different wavelengths. This allows the image to be digitized into two separate images, one in which all the cell nuclei are optically enhanced (ethyl green or Fast Green) and one in which only those tissue areas with receptor staining (DAB) are optically enhanced. In a preferred embodiment, the images can be separated by a 600 nanometer (red) filter to produce an image of all of the counter stained area, and a 500 nanometer (green) filter to produce an image of only those tissue areas with the DAB precipitate staining.

To further differentiate those areas, an interactive threshold setting technique can be used where an operator visualizing the images can set a boundary on the areas under consideration. When the boundaries are set, the images are formed by eliminating all parts of the image that are below the thresholds in optical density. A threshold may be set for the first image, and a second threshold may be set for the second image.

The image processing method then consists of first forming the mask image of the tissues under consideration with the red filter. This mask image may be stored and another image for expressed protein quantification may then acquired by using the green filtered version of the same image. The effect of the filters in combination is to optically enhance (make darker) those areas of the tissue mask where tissue components are stained with DAB and to make lighter those tissue components with only green counterstain. An image analysis can then be performed using only those areas of the image that are stained and which are within the mask.

Red and green filters are suitable for practice of the disclosure as well as DAB and green counterstain. This implementation shows a convenient and advantageous method for discriminating between two areas having counterstaining. It is recognized that there are various other staining or optical enhancement methods and filtering methods which can be used to optically enhance one particular area or feature over another cell feature such as Fast green, eosin, and the like.

Following immunohistochemical staining, the optical image of the tissue or cell sample generated by the computer-aided image analysis system may then magnified under a light microscope and separated into a pair of images. Such equipment can include a light or fluorescence microscope, and image-transmitting camera and a view screen, most preferably also comprising a computer that can be used to direct the operation of the device and store and manipulate the information collected, most preferably in the form of optical density of certain regions of a stained tissue preparation. Image analysis devices useful in the practice of this disclosure include but are not limited to the CAS 200 (Becton Dickenson, Mountain View, Calif.), Chromavision or Tripath systems. The separated images may be enhanced using a pair of optical filters, one having a maximum absorption corresponding to the stain and the other having a maximum absorption corresponding to the counterstain. In other embodiments of the method of the present disclosure, a plurality of image analysis filters may be used to detect, differentiate, and quantitate the level of staining of different cellular proteins in various components (e.g., membrane, cytoplasm, and nucleus). In preferred embodiments, specific staining for PIK3CA may be detected, measured and quantitated using image analysis equipment, defined herein as comprising a light or fluorescence microscope, and image-transmitting camera and a view screen, most preferably also comprising a computer that can be used to direct the operation of the device and also store and manipulate the information collected, most preferably in the form of optical density of certain regions of a stained tissue preparation. Image analysis devices useful in the practice of this disclosure include but are not limited to the CAS 200 system (Becton Dickenson, Mountain View, Calif.). From a digitized image, a nuclear or cytoplasmic image mask may be formed by forming the image at one wavelength of light such as red wavelength or green optical filter. The tissue mask may be stored and a second filter may be used to form another filtered image of the areas with the optical enhancement factor. Differentiation of cellular characteristics can be made by comparing the first image with the second image to obtain a quantification of material stained with the optical enhancement factor and thus, an assay of the amount of the particular target under study.

After immunohistochemical staining, a quantified measure of the percentage of cells expressing PIK3CA can be taken by digitizing microscope images of stained samples, and converting light intensity values in each picture element (pixel) of the digitized image to optical density values, which correspond to the percentage of stained cell nuclei. More specifically, computerized image analysis can be used to determine from a digital grey scale image, a quantity of cells having a particular stain. The grey scale images are representative of the amount of an optical enhancement factor, such as a chromagen, which binds to a specific target under study and thereby allows optical amplification and visualization of the target.

The present disclosure also includes methods for fixing cells and tissue samples for analysis. Generally, neutral buffered formalin may be used. Any concentration of neutral buffered formalin that can fix tissue or cell samples without disrupting the epitope can be used. Preferably, the method includes suitable amounts of phosphatase inhibitors to inhibit the action of phosphatases and preserve phosphorylation. Any suitable concentration of phosphatase inhibitor can be used so long as the biopsy sample is stable and phosphatases are inhibited, for example 1 mM NaF and/or $Na_3VO_4$ can be used. In one method a tissue sample or tumor biopsy (e.g., biological sample) may be removed from a patient and immediately immersed in a fixative solution which can and preferably does contain one or more phosphatase inhibitors, such as NaF and/or $Na_3VO_4$. Preferably, when sodium orthovanadate is used it is used in an activated or depolymerized form to optimize its activity. Depolymerization can be accomplished by raising the pH of its solution to about 10 and boiling for about 10 minutes. The phosphatase inhibitors can be dissolved in the fixative just prior to use in order to preserve their activity. Fixed samples can then be stored for several days or processed immediately. To process the samples into paraffin after fixing, the fixative can be thoroughly rinsed away from the cells by flushing the tissue with water. The sample can be processed to paraffin according to normal histology protocols which can include the use of reagent grade ethanol. Samples can be stored in 70% ethanol until processed into paraffin blocks. Once samples are processed into paraffin blocks they can be analyzed histochemically for virtually any antigen that is stable to the fixing process.

In practicing the method of the present disclosure, staining procedures can be carried out by a technician in the laboratory. Alternatively, the staining procedures can be carried out using automated systems. In either case, staining procedures for use according to the methods of this disclosure are performed according to standard techniques and protocols well-established in the art.

The amount of mutant PIK3CA can be quantitated by image analysis in the biological sample. For example, the amount of the expression of mutant PIK3CA may be quantitated from an average optical density (OD) of expression of mutant PIK3CA in a defined cellular area. Alternatively, the amount of the expression of mutant PIK3CA may be quantitated from an average OD determined on a per cell basis in the defined cellular area. The average OD on a per cell basis may be obtained by dividing the average OD for the defined cellular area by a number of nuclei in the defined cellular area.

Three parameters may be established in order to validate an immunohistochemistry assay including, for example, sensitivity, specificity and/or reproducibility.

For sensitivity analysis, a known tissue type or cell line that expresses the target should be used to optimize the antibody dilution. For tissue, it may be useful if a particular cell type within the tissue expresses the target, while another particular cell does not (e.g. adrenal gland would be useful if a target was expressed in cortical cells but not medullar cells, or vice versa). For the assay to be acceptable, target localization should correspond to what may be stated in the package insert (if given), the accepted literature or other appropriate reference site.

For specificity analysis, the antibody should provide robust staining of the target in the appropriate tissue or cell type with minimal to no background staining of cell types or structures that do not express the target. If the antibody is suitable for western blotting, a cell line that expresses the target can be analyzed. The presence of a single band of the expected molecular weight of the target would indicate that the antibody is specific for the target. Even further proof of specificity, if possible, would be to treat the cells with an agent that modulates the expression of the target or identify a cell line that does not express the target at all. However, this is not always possible, especially if the target is highly or ubiquitously expressed (e.g. 4E-BP1).

For reproducibility analysis, inter-assay reproducibility may be evaluated by staining several positive tissues in 3 consecutive runs (usually performed on different days). Immunohistochemistry assays should be worked up on an automated staining system when possible (e.g. Dako Autostainer) to reduce variability.

Protein Based Assays

The expression level of mutant PIK3CA in a biological sample may be determined by immunohistochemically staining cells in the sample using a detectably-labeled agent (e.g., an antibody) specific for mutant PIK3CA. Mutant PIK3CA expression may be quantified at the protein level using methods known in the art, for example using quantitative enzyme linked immunosorbent assays ("ELISA"). Methods for designing and using quantitative ELISA assays are well known in the art. These methods require use of monoclonal or polyclonal antibodies that are specific for the mutant PIK3CA protein.

Suitable monoclonal antibodies may be prepared by standard hybridoma methods, using differential binding assays to ensure that the antibodies are specific for mutant PIK3CA and do not show cross-reactivity between related proteins. Alternatively, suitable monoclonal antibodies may be prepared using antibody engineering methods such as phage display. Methods for obtaining highly specific antibodies from antibody phage display libraries are known in the art, and several phage antibody libraries are commercially available from, for example, MorphoSys (Martinsried, Germany), Cambridge Antibody Technology (Cambridge UK) and Dyax (Cambridge Mass.). Suitable phage display methods are described, for example, in U.S. Pat. Nos. 6,300,064 and 5,969,108; "Antibody Engineering," McCafferty et al. (Eds.) (IRL Press 1996)). Once the antibody heavy and light chain genes are recovered from the phage antibodies, antibodies in any suitable format may be prepared, e.g. whole antibodies, Fab, scFv, etc.

Other antibody preparations may also be used, for example *Camelid* antibodies, which contain only heavy immunoglobulin chains (e.g., Muyldermans et al. *J. Biotechnol.* June; 74(4):277-302 (2001)). Other antibody formats are described, for example in "Antibody Engineering," McCafferty et al. (Eds.) (IRL Press 1996).

Polyclonal antibodies specific for mutant PIK3CA may also be prepared using traditional animal-based methods. Peptides derived from mutant PIK3CA can be conjugated at their N- or C-termini to carrier proteins such as bovine serum albumin (BSA) or keyhole limpet hemocyanin (KLH) and used to immunize animals, such as rabbits, using well-known immunization regimes. Specific polyclonal antibodies can be obtained from the serum of the animal by, for example, affinity chromatography over a matrix containing the peptide used for immunization bound to a solid support.

An ELISA assay may be used to quantitate the level of expression of mutant PIK3CA. Many ELISA applications and formats have been described. Various sources provide discussion of ELISA chemistry, applications, and detailed protocols (e.g., Crowther, "Enzyme-Linked Immunosorbent Assay (ELISA)," in Molecular Biomethods Handbook, Rapley et al., pp. 595-617, Humana Press, Inc., Totowa, N.J. (1998); Harlow and Lane (eds.), Antibodies. A Laboratory Manual, Cold Spring Harbor Laboratory Press (1988); Ausubel et al. (eds.), Current Protocols in Molecular Biology, Ch. 11, John Wiley & Sons, Inc., New York (1994); and Laurino et al. Ann. Clin. Lab Sci., 29(3):158-166 (1999)).

In one embodiment of the present disclosure, an ELISA based method may be provided in which an antibody specific for mutant PIK3CA may be first immobilized on a solid support (e.g. in a microtiter plate well). Protein samples may then added to the plate from either a control or biological sample containing mutant PIK3CA. Mutant PIK3CA is then bound to antibody and can be detected and quantitated by the use of an antibody-enzyme conjugate capable of binding to another region of mutant PIK3CA (not bound by the first antibody) and producing a quantifiable signal. In some embodiments, the amount of antigen present may be directly proportional to the amount of enzyme reaction product produced after the addition of an appropriate enzyme substrate.

As indicated previously, enzymes commonly used in ELISAs include horseradish peroxidase (HRPO), urease, alkaline phosphatase, glucoamylase and β-galactosidase. Protocols for the preparation of suitable antibody-enzyme conjugates are well known in the art. The present disclosure provides methods for the preparation of an antibody-enzyme (i.e., HRPO enzyme) conjugate that specifically recognizes the antigens of interest (i.e., PIK3CA) for use in an immunoassay (e.g., ELISA). The method provided herein, as those of skill in the art will recognize other methods for antibody-enzyme conjugation that find use with the present disclosure.

Conjugation of enzymes to antibodies involves the formation of a stable, covalent linkage between an enzyme (e.g., HRPO or alkaline phosphatase) and the antibody (e.g., the anti-PIK3CA antibody), where neither the antigen-binding site of the antibody nor the active site of the enzyme is functionally altered.

The conjugation of antibody and HRPO is dependent on the generation of aldehyde groups by periodate oxidation of the carbohydrate moieties on HRPO (Nakane and Kawaoi, J. Histochem. Cytochem., 22:1084-1091 (1988)). Combination of these active aldehydes with amino groups on the antibody forms Schiff bases that, upon reduction by sodium borohydride, become stable.

Protocols to make antibody-enzyme conjugates using urease or alkaline phosphatase enzymes are also known in the art (Healey et al., Clin. Chim. Acta 134:51-58 (1983); Voller et al., Bull. W.H.O., 53:55-65 (1976); and Jeanson et al., J. Immunol. Methods 111:261-270 (1988)). For urease conjugation, cross-linking of the urease enzyme (e.g., Urease Type VII, Sigma No. U0376) and antibody using m-maleimidobenzoyl N-hydroxysuccinimide ester (MBS) is achieved through benzoylation of free amino groups on the antibody. This may be followed by thiolation of the maleimide moiety of MBS by the cysteine sulfhydryl groups of urease. To prepare an alkaline phosphatase-antibody conjugate, a one-step glutaraldehyde method is the simplest procedure (Voller et al. Bull. W.H.O., 53:55-65 (1976)). This antibody-alkaline phosphatase conjugation protocol uses an enzyme immunoassay grade of the alkaline phosphatase enzyme.

The end product of an ELISA is a signal typically observed as the development of color or fluorescence. Typically, this signal may be read (i.e., quantitated) using a suitable spectrocolorimeter (i.e., a spectrophotometer) or spectrofluorometer. The amount of color or fluorescence may be directly proportional to the amount of immobilized antigen. In some embodiments of the present disclosure, the amount of antigen in a sample (e.g., the amount of PIK3CA) is quantitated by comparing results obtained for the sample with a series of control wells containing known concentrations of the antigen (i.e., a standard concentration curve). A negative control may also be included in the assay system.

It is contemplated that any suitable chromogenic or fluorogenic substrates may find use with the enzyme-conjugated antibodies of the present disclosure. In some embodiments of the present disclosure, the substrate p-nitrophenyl phosphate (NPP) in diethanolamine may be the preferred substrate for use in colorimetric ELISA methods, and 4-methylumbelliferyl phosphate (MUP) may be the preferred alkaline phosphatase substrate in fluorometric ELISA methods. Conjugated antibodies can include radioisotopes, fluorophores, enzymes, luminescers, or visible particles (e.g., colloidal gold and dye particles). These and other labels are well known in the art and are described, for example, in the following U.S. Pat. Nos. 3,766,162; 3,791,932; 3,817,837; 3,996,345; and 4,233,402.

The present disclosure provides various ELISA protocols for the detection and/or quantitation of PIK3CA. In one embodiment, the present disclosure provides a "direct ELISA" for the detection of PIK3CA. In some embodiments, the antigen of interest in a sample (i.e., PIK3CA) may be bound (along with unrelated antigens) to the solid support (e.g., a microtiter plate well). The immobilized antigen may then be directly detected by the antigen-specific enzyme-conjugated antibody, also provided by the present disclosure. Addition of an appropriate detection substrate results in color development or fluorescence that may be proportional to the amount of PIK3CA present in the well.

In another embodiment, the present disclosure provides an indirect ELISA for the detection of mutant PIK3CA in a sample. In this embodiment, antigen of interest in a sample may be immobilized (along with unrelated antigens) to a solid support (e.g., a microtiter plate well) as in the direct ELISA, but is detected indirectly by first adding an antigen-specific antibody, then followed by the addition of a detection antibody specific for the antibody that specifically binds the antigen, also known as "species-specific" antibodies (e.g., a goat anti-rabbit antibody), which are available from various manufacturers known to one in the art (e.g., Santa Cruz Biotechnology; Zymed; and Pharmingen/Transduction Laboratories).

In another embodiment, the present disclosure provides "sandwich ELISA" methods, in which the antigen in a sample may be immobilized on a solid support by a "capture antibody" that has been previously bound to the solid support. In general, the sandwich ELISA method is more sensitive than other configurations, and may be capable of detecting 0.1-1.0 ng/ml protein antigen. As indicated above, the sandwich ELISA method involves pre-binding the "capture antibody" which recognizes the antigen of interest (i.e., mutant PIK3CA) to the solid support (e.g., wells of the microtiter plate). In some embodiments, a biotinylated capture antibody may be used in conjunction with avidin-coated wells. Test samples and controls may then beaded to the wells containing the capture antibody. If antigen is present in the samples and/or controls, it is bound by the capture antibody.

In some embodiments, after a washing step, detection of antigen that has been immobilized by the capture antibody may be detected directly (i.e., a direct sandwich ELISA). In other embodiments detection of mutant PIK3CA that has been immobilized by the capture antibody may be detected indirectly (i.e., an indirect sandwich ELISA). In the direct sandwich ELISA, mutant PIK3CA may be detected using a specific enzyme-conjugated antibody. In the indirect sandwich ELISA, mutant PIK3CA is detected by using an antibody specific for mutant PIK3CA, which may then be detected by another enzyme-conjugated antibody which binds the antigen-specific antibody, thus forming an antibody-antigen-antibody-antibody complex. In both the direct and indirect sandwich ELISAs, addition of a suitable detection substrate results in color development or fluorescence that is proportional to the amount of mutant PIK3CA that is present in the well.

In the sandwich ELISA, the capture antibody used may be typically different from the second antibody (the "detection antibody"). The choice of the capture antibody may be empirical, as some pairwise combinations of capture antibody and detection antibody are more or less effective than other combinations. The same monoclonal antibody must not be used as both the capture antibody and the conjugated detection antibody, since recognition of a single epitope by the capture antibody will preclude the enzyme-conjugated detection antibody from binding to the antigen. However, in some embodiments, two different monoclonal antibodies that recognize different epitopes may be used in this assay. In other embodiments, the same polyclonal antibody preparation is used as both the capture antibody and conjugated detection antibody, since multiple epitopes are recognized in the pool of polyclonal antibody species. In some embodiments, the polyclonal anti-PIK3CA antibodies provided by the present disclosure may be used as both the capture antibody and the enzyme-conjugated detection antibody in the sandwich ELISA.

Furthermore, it is not intended that the present disclosure be limited to the direct ELISA and sandwich ELISA protocols particularly described herein, as the art knows well numerous alternative ELISA protocols that also find use in the present disclosure (See, e.g., Crowther, "Enzyme-Linked Immunosorbent Assay (ELISA)," in Molecular Biomethods Handbook, Rapley et al., pp. 595-617, Humana Press, Inc., Totowa, N.J. (1998); and Ausubel et al. (eds.), Current Protocols in Molecular Biology, Ch. 11, John Wiley & Sons, Inc., New York (1994)). Thus, any suitable ELISA method including, but not limited to, competitive ELISAs also may find use with the present disclosure.

In yet a further embodiment of the present disclosure, an ELISA amplification system may be provided. These amplification systems produce at least 10-fold, and more preferably, a 500-fold increase in sensitivity over traditional alkaline phosphatase-based ELISAs. In one preferred embodiment of the ELISA amplification protocol, bound alkaline phosphatase acts on an NADPH substrate, whose reaction product initiates a secondary enzymatic reaction resulting in a colored product. Each reaction product from the first reaction initiates many cycles of the second reaction in order to amplify the signal (See e.g., Bio-Rad ELISA Amplification System, Cat. No. 19589-019).

In yet another embodiment of the present disclosure, expression of PIK3CA may be measured and quantitated by Western Blot analysis. Briefly, proteins samples may be electrophoresed on an acrylamide gel and transferred to a membrane such as nitrocellulose or PVDF. The blot may be detected with an antibody specific for PIK3CA. These primary antibodies may then be detected, for example, with labeled secondary antibodies. The fluorescence intensity of the dye may be measured for both a test and control sample and the ratio of the intensity indicates the ratio of the two proteins.

RNA Based Assays

Mutant PIK3CA gene expression may be determined by methods which detect particular mRNAs in cells. These include, hybridization assays using complementary DNA probes (such as in situ hybridization using labeled mutant PIK3CA and/or PIK3CA riboprobes, Northern blot and related techniques) and various nucleic acid amplification assays (such as RT-PCR using complementary primers specific for PIK3CA, and other amplification type detection methods, such as, for example, branched DNA, SISBA, TMA and the like). Protocols for the detection of specific mRNAs in a sample are well known in the art (Sambrook et al., (1990) Molecular Cloning—A Laboratory Manual, Cold Spring Harbor Laboratory Press; Ausubel et al., (1998) Current Protocols in Molecular Biology, Wiley).

In one embodiment of the present disclosure, mutant PIK3CA gene expression may be quantified at the RNA level by amplification of mutant PIK3CA RNA by, for example, reverse transcription polymerase chain reaction (RT-PCR) and resolution/quantification of the reaction products by gel electrophoresis (e.g., slab, capillary, etc.) and product measurement (e.g., by scanning, laser, etc.). Those of skill in the art will appreciate that many variations of the technique may be possible.

In another embodiment of the present disclosure, mutant PIK3CA gene expression may be measured by a real-time quantitative RT-PCR based method. Methods for carrying out quantitative PCR are known in the art (e.g., U.S. Pat. Nos. 5,210,015 and 5,487,972 and EP 512334B1). Commercial instruments for carrying out quantitative PCR and RT-PCR are available from PE Applied Biosystems (Foster City, Calif.), from Roche Molecular Systems, Inc. (Alameda, Calif.), and from Roche Molecular Biochemicals (Indianapolis, Ind.).

The primers used for PCR may be suitably designed to comprise nucleotide sequences which encode amino acid sequences that are highly conserved within the mutant PIK3CA gene. Methods to identify nucleotide sequences corresponding to a given amino acid sequence include deduction on the basis of the codon usage of the host cell, and methods of making mixed oligonucleotide sequences using multiple codons (hereinafter referred to as a 'degenerate oligonucleotides'). In the latter case, the multiplicity of oligonucleotides can be reduced by introducing hypoxanthine to their nucleotide sequences.

Primers for PCR amplification of the mutant PIK3CA gene may comprise a nucleotide sequence designed to anneal with a template chain, the primer being joined to an additional 5' sequence. The choice of such an additional 5' nucleotide sequence may not be particularly limited, as long as the primer can be used for PCR or RT-PCR. Such an additional 5' sequence can be, for example, a nucleotide sequence convenient for the cloning operation of a PCR product. Such a nucleotide sequence can be, for example, a restriction enzyme cleavage site or a nucleotide sequence containing a restriction enzyme cleavage site.

Furthermore, in designing of the primer for PCR it may be preferred that the sum of the number of guanine (G) and the number of cytosine (C) bases is 40 to 60% of the total number of bases. Furthermore, there is little or no self-annealing for a given primer and, in the case of a pair of primers, little or no annealing between the primers.

The number of nucleotides making up the primer for PCR amplification of the PIK3CA gene is not particularly limited, as long as it can be used for PCR. The lower limit of the number is generally 10 to 14 nucleotides, with the upper limit 40 to 60 nucleotides. The primers may be 14 to 40 oligonucleotides in length.

The primers for PCR amplification of the mutant PIK3CA gene may be preferably DNA. Nucleosides in the primer can be deoxy adenosine, deoxy cytidine, deoxy thymidine, and deoxy guanosine, and additionally deoxy inosine. The 5'-position of the nucleoside at the 5'-end of the primer for PCR is suitably a hydroxyl group or a hydroxy group to which one phosphoric acid is bonded by an ester link.

Synthesis of primer for PCR amplification of the mutant PIK3CA gene can be performed by methods generally used for synthesis of nucleic acids, for example, the phosphoamidite method. An automated DNA synthesizer can be preferably used in such a method.

Relative quantitation of mutant PIK3CA mRNA may be achieved by means of the ABI Prism 7700 Sequence Detection System (Applied Biosystems, Foster City, Calif.). In TaqMan real-time quantitation technology, the 5'exonuclease activity of the Taq polymerase cleaves and releases a hybridization probe that is labeled with a fluorescent reporter dye. This fluorogenic probe is specific for the target sequence, thereby generating a fluorescence signal that is specific and is directly proportional to the amount of PCR product synthesized. PCR reactions are characterized by the time-point during cycling when amplification of the PCR product is first detected, rather than the amount of product accumulated after a fixed number of cycles. Since the amount of product at the exponential phase of the PCR is proportional to the initial copy number of the target, the more abundant the starting quantity of a target, the earlier will the PCR amplification be detected by means of the fluorescence signal. In this technology, the target quantity is measured by identifying the threshold cycle number ($C_T$), i.e. when the fluorescence signal crosses a preset detection threshold. The laser detector of the Prism 7700 monitors the cycle to cycle change in fluorescence signal on-line. The fewer cycles it takes to reach a detectable level of fluorescence, the greater the initial copy number.

In another embodiment, an oligonucleotide ligation assay (OLA) (e.g., U.S. Pat. No. 4,998,617) may be used. The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides hybridize such that their termini abut, and create a ligation substrate. Ligation then permits the labeled oligonucleotide to be recovered using avidin, or another biotin ligand. Nickerson, D. A. et al. ((1990) *Proc. Natl. Acad. Sci. USA* 87:8923-27) have described a nucleic acid detection assay that combines attributes of PCR and OLA. In this method, PCR may be used to achieve the exponential amplification of target DNA, which is then detected using OLA.

Several techniques based on this OLA method have been developed and may be useful for detecting RNA. For example, U.S. Pat. No. 5,593,826, discloses an OLA using an oligonucleotide having 3'-amino group and a 5'-phosphorylated oligonucleotide to form a conjugate having a phosphoramidate linkage. In another variation of OLA described in To be et al. ((1996), *Nucleic Acids Res.* 24: 3728), OLA combined with PCR may permit the detection and quantification of PIK3CA RNA in a single microtiter well.

In another embodiment, PIK3CA RNA levels are quantified by in situ detection according to standard methods.

In yet a further embodiment of the disclosure, probes capable of hybridizing specifically to PIK3CA RNA, are attached to a solid phase support, e.g., a "chip," "DNA probe array" or "nucleic acid probe array" and used to quantitate PIK3CA expression. Oligonucleotides can be bound to a solid support by a variety of processes, including lithography. For example, a chip can hold up to about 250,000 oligonucleotides. The solid phase support may then be contacted with a test nucleic acid and hybridization to the specific probes is detected. Accordingly, the quantification of numerous samples (e.g., different tissues from the same individual or samples from different individuals) or the profiling of the RNA levels of a gene can be identified in a single hybridization experiment.

Methods for Predicting Responsiveness to a Receptor Tyrosine Kinase Inhibitor

The present disclosure includes methods for predicting responsiveness of a subject with a disease or disorder to a receptor tyrosine kinase inhibitor by obtaining the biological sample (e.g., a formalin fixed paraffin embedded tissue) comprising one or more tumor cells and one or more normal cells from the subject; assaying the biological sample by an immunohistochemistry (IHC) based technique for expression of mutant PIK3CA using an antibody specific for mutant PIK3CA; quantitating an amount of mutant PIK3CA expression in the one or more tumor cells and an amount of mutant PIK3CA expression in the one or more normal cells; comparing the amount of mutant PIK3CA expression in the tumor cells to the amount of PIK3CA expression in the normal cells; determining that mutant PIK3CA is elevated in the tumor cells where the amount of expression of mutant PIK3CA is greater in the tumor cells as compared to the normal cells or determining that expression of mutant PIK3CA is reduced in the tumor cells where the amount of expression of mutant PIK3CA is less in the tumor cells than in the normal cells; and predicting that the subject is responsive to a receptor tyrosine kinase inhibitor where expression of mutant PIK3CA in the tumor cells is less than expression of mutant PIK3CA in the normal cells or determining that the subject is not responsive to a receptor tyrosine kinase inhibitor where expression of mutant PIK3CA in the tumor cells is the same or greater than expression of mutant PIK3CA in the normal cells. The subject may be predicted to be responsive to the receptor tyrosine kinase inhibitor where the amount of mutant PIK3CA detected and quantitated in the biological sample is less than the amount of mutant PIK3CA detected in normal cells obtained from the same subject from which the biological sample was obtained or a different subject from which the biological sample was obtained.

In some embodiments, the subject may be predicted to be responsive to a receptor tyrosine kinase inhibitor where the amount of mutant PIK3CA expressed in tumor cells in the biological sample is less than 5%, 10%, 15%, 20%, 25%, 30%, 35%, 40%, 45%, 50%, 55%, 60%, 65%, 70%, 75%, 80%, 85%, 90%, 95% or 100% of the amount of PIK3CA detected in the normal cells in the biological sample. Alternatively, a subject may be predicted to be responsive to the receptor tyrosine kinase inhibitor where the amount of mutant PIK3CA expressed in tumor cells is above or below a set threshold. For example, a threshold may be set at the maximum amount of mutant PIK3CA expressed in a tumor cells from a biological sample obtained from a subject where the subject is responsive to treatment with a receptor tyrosine kinase inhibitor. Such a threshold may be an average obtained from two or more subjects.

In some embodiments, the receptor tyrosine kinase inhibitor may be an antibody including, for example, a monoclonal antibody. Monoclonal antibodies may include, but are not limited to cetuximab (Erbitux®), panitumumab, zalutumumab, nimotuzumab or matuzumab. In other embodiments, the receptor tyrosine kinase inhibitor is a small molecule inhibitor. Small molecule inhibitors may include, but are not limited to, gefitinib, erlotinib or lapatinib.

A determination of whether a subject will be predicted to be responsive to a receptor tyrosine kinase inhibitor may be used to direct a therapeutic regimen for a particular disease or disorder including, for example, cancer. Such methods may comprise obtaining the biological sample (e.g., a formalin fixed paraffin embedded tissue) comprising one or more tumor cells and one or more normal cells from the subject; assaying the biological sample by an immunohistochemistry (IHC) based technique for expression of mutant PIK3CA using an antibody specific for mutant PIK3CA; quantitating an amount of mutant PIK3CA expression in the one or more tumor cells and an amount of mutant PIK3CA expression in the one or more normal cells; comparing the amount of mutant PIK3CA expression in the tumor cells to the amount of mutant PIK3CA expression in the normal cells; determining that mutant PIK3CA is elevated in the tumor cells where the amount of expression of mutant PIK3CA is greater in the tumor cells as compared to the normal cells or determining that expression of mutant PIK3CA is reduced in the tumor cells where the amount of expression of mutant PIK3CA is less in the tumor cells than in the normal cells; and predicting that the subject is responsive to a receptor tyrosine kinase inhibitor where mutant PIK3CA expression in the tumor cells is less than mutant PIK3CA expression in the normal cells or determining that the subject is not responsive to a receptor tyrosine kinase inhibitor where mutant PIK3CA expression in the tumor cells is the same or greater than mutant PIK3CA expression in the normal cells.

EXAMPLES

Example 1

IGF1R Signaling in PIK3CA Mutant Cells

A time-course study was performed comparing wild-type and mutant PIK3CA cell lines to understand the kinetics of IGF-IR activation in differing genetic backgrounds.

Figure 1:
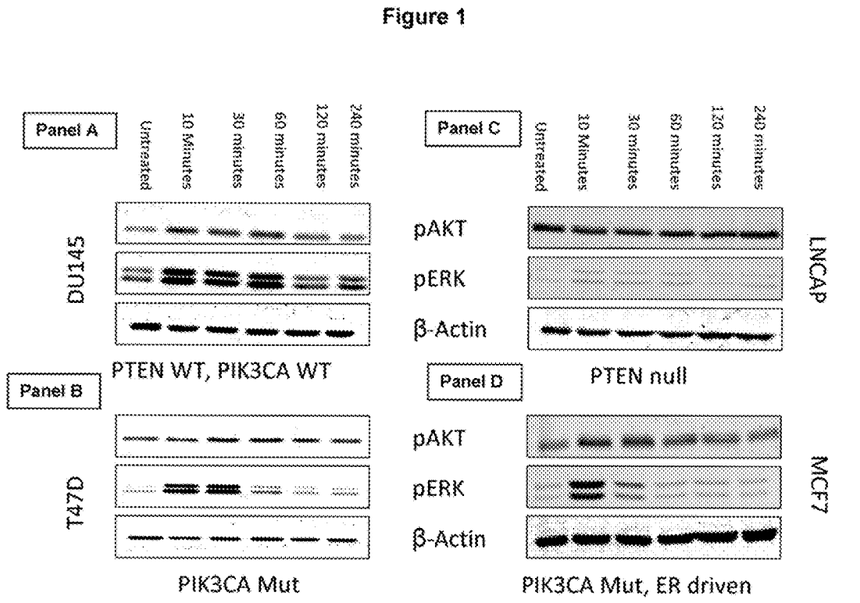
FIG. 1 shows the kinetics of PI3K activation by IGF-1 in cells harboring mutations in the PI3K pathway: Four cell lines either wild-type or harboring PIK3CA or PTEN mutations were serum starved overnight followed by treatment with 25 ng/ml IGF-I for 10 minutes. Panel (A) shows pAKT and pErk1/2 expression in DU145 cells; Panel (B) shows pAKT and pErk1/2 expression in T47D cells; Panel (C) shows pAKT and pErk1/2 expression in LNCAP cells and Panel (D) shows pAKT and pErk1/2 expression in MCF7 cells, after treatment of the cells with IGF-1 ligand.

Briefly, four cell lines either wild-type (DU145) or harboring PIK3CA (MCF7 and T47D) or PTEN (LNCAP) mutations were serum starved overnight followed by treatment with 25 ng/ml IGF-1 for 10 minutes. MCF7 cells are known to have an E545K mutation in PIK3CA and T47D cells are known to have a E545K mutation in PIK3CA. Cells from each cell line were then either harvested for whole cell extracts or replenished with 1.0% FBS containing media without exogenous IGF-1 and harvested for whole cell extracts at various time points thereafter. This approach allowed an analysis of the duration of IGF1R signaling after a transient activation of the IGF1R receptor. Lysates from each of the tested cells lines were then analyzed by Western blot for expression of pAkt and pErk1/2. Unexpectedly, cell lines that harbor PIK3CA activating mutations demonstrate shorter activation times to IGF-1 and have a low basal level pAkt and pErk1/2 that is activated by IGF-1 (see, e.g., FIG. 1, Panels B and D) as compared to those cells lines that harbor wild-type PIK3CA (see, FIG. 1, Panel A).

Figure 2:
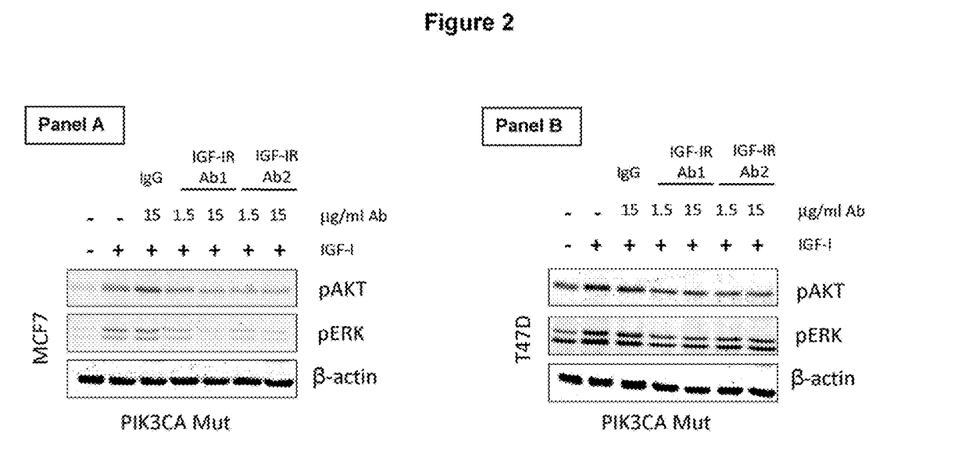
FIG. 2 shows the kinetics of PI3K activation by IGF-1 in cells harboring mutations in the PI3K pathway and treated with an antibody to IGF1R. Cells were serum starved 18 hours with the addition of IGF1R antibodies followed by 75 ng/ml IGF-1 for 15 minutes before harvest of whole cell extracts. Panel (A) shows pAKT and pErk1/2 expression in MCF7 cells treated with two different antibodies to IGF1R; Panel (B) shows pAKT and pErk1/2 expression in T47D cells treated with two different antibodies to IGF1R; and Panel (C) shows pAKT and pErk1/2 expression in DU145 cells treated with two different antibodies to IGF1R.

As shown above, breast tumor cell lines that harbor activating PIK3CA mutations (MCF7 and T47D) exhibit low baseline levels of pAkt that were inducible upon the addition of the IGF1R ligand IGF-I (see, FIG. 2, Panels A and B). This induction of pAkt was subsequently reduced with pre-treatment of the cells with an IGF1R inhibiting antibody. Notably, the IGF-I induced activation of pERK was not reduced in the PIK3CA wild-type DU145 tumor cell line. Therefore, tumors that harbor activating mutations in the PIK3CA gene are dependent on the IGF-1 pathway and inhibition of this pathway through the upstream IGF1R, by an antibody or small molecule inhibits downstream signaling and tumor cell proliferation.

Example 2

Determining Responsiveness to IGF1R Inhibitor

The success of therapeutics in medicine and especially in a complex disease such as cancer depends on the correct diagnosis choice of patients treated with the drug. This process requires knowledge of the specific patient markers that can be used to predict how the patient will respond to a given drug or class of drugs that share a common mechanism of action. The inventor of the instant application has shown that patients with expression levels of mutant PIK3CA do not respond to treatment with the receptor tyrosine kinase inhibitor such as an IGF1R inhibitor while patients not expressing a mutant PIK3CA did respond to treatment with the receptor tyrosine kinase inhibitor such as an IGF1R inhibitor. A mammalian tumor likely to be responsive to an IGF1R inhibitor may be identified as follows.

Briefly, a biological sample was removed from a patient prior to treatment with a receptor tyrosine kinase inhibitor such as an IGF1R inhibitor and analyzed by IHC analysis to characterize the protein expression levels for one or more mutant forms of PIK3CA, including, one or more mutations in PIK3CA are selected from the group consisting of: E542K, E545K, E545G, E545D, Q546K, Q546R, M1043I, M1043V, H1047R, H1047L, H1047Y, G1049R and G1049S. The patient sample may consist of a tumor resection, tumor biopsy, tumor needle biopsy, fine needle aspirant, or other means of isolating cancerous cells for the patient. In an exemplary embodiment, the biological samples were analyzed by conventional IHC analysis followed by manual scoring (0-3 scale based upon staining intensity and number of cells staining) and automated scoring based upon computer methods to determine staining intensity over a designated area. The results of the IHC analysis were then used to determine if the patient was likely to be responsive to treatment with a receptor tyrosine kinase inhibitor such as an IGF1R inhibitor. Patients in which a biological sample was obtained that expresses a PIK3CA mutation are predicted to not respond to treatment with a receptor tyrosine kinase inhibitor while patients that do not express a PIK3CA mutation are predicted to respond to treatment with a receptor tyrosine kinase inhibitor.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

The invention claimed is:

1. A method of contacting a cell with an antibody specific for insulin-like growth factor 1 receptor (IGF1R), the method comprising:

a. obtaining a cell;
b. assaying the cell for one or more PIK3CA mutations;
c. determining if one or more PIK3CA mutations are present in the cell;

d. employing the determination of one or more PIK3CA mutations in the cell to predict responsiveness of the cell to the antibody, wherein the presence of one or more PIK3CA mutations in the cell predicts that the cell will be responsive to the antibody; and e. selectively contacting a cell predicted to be responsive to the antibody with the antibody.

2. The method of claim 1, wherein PIK3CA has the amino acid sequence set forth in SEQ ID NO: 1.

3. The method of claim 2, wherein the one or more mutations in PIK3CA are selected from the group consisting of: E542K, E545K, E545G, E545D, Q546K, Q546R, M1043I, M1043V, H1047R, H1047L, H1047Y, G1049R and G1049S.

4. The method of claim 1, wherein the cell is assayed for PIK3CA mutations by analyzing nucleic acid obtained from the cell.

5. The method of claim 1, wherein the antibody is a monoclonal antibody.

6. The method of claim 1, wherein the cell is from a tumor biopsy.

7. The method of claim 1, wherein the cell is from an aspirate.

8. The method of claim 1, wherein the cell is from a cancer patient.

9. A method for treating a subject with cancer with an antibody specific for IGF1R, the method comprising:
   a. obtaining a biological sample from the subject;
   b. assaying the biological sample for one or more PIK3CA mutations;
   c. determining if one or more PIK3CA mutations are present in the biological sample;
   d. employing the determination of one or more PIK3CA mutations in the cell to predict responsiveness of the subject to the antibody, wherein the presence of one or more PIK3CA mutations in the biological sample predicts that the subject will be responsive to the antibody; and
   e. administering a therapeutically effective amount of the antibody to the subject predicted to be responsive to the IGF1R antibody with the antibody to treat the cancer.

10. The method of claim 9, wherein PIK3CA has the amino acid sequence set forth in SEQ ID NO: 1.

11. The method of claim 10, wherein the one or more mutations in PIK3CA are selected from the group consisting of: E542K, E545K, E545G, E545D, Q546K, Q546R, M1043I, M1043V, H1047R, H1047L, H1047Y, G1049R and G1049S.

12. The method of claim 9, wherein the biological sample is assayed for PIK3CA mutations by analyzing nucleic acid obtained from the sample.

13. The method of claim 9, wherein the biological sample is assayed for PIK3CA mutations by analyzing proteins obtained from the sample.

14. The method of claim 12, wherein the cancer is breast cancer.

15. The method of claim 9, wherein the antibody is a monoclonal antibody.

16. The method of claim 9, wherein the biological sample is a tumor biopsy.

17. The method of claim 9, wherein the biological sample is an aspirate.

18. A method for selecting a subject with cancer for treatment with an antibody specific for IGF1R, the method comprising:
   a. obtaining a biological sample from the subject;
   b. assaying the biological sample for one or more PIK3CA mutations;
   c. determining if one or more PIK3CA mutations are present in the biological sample;
   d. employing the determination of one or more PIK3CA mutations in the cell to predict responsiveness of the subject to the antibody, wherein the presence of one or more PIK3CA mutations in the biological sample predicts that the subject will be responsive to the antibody; and
   e. selecting the subject predicted to be responsive to the IGF1R antibody for treatment with a therapeutically effective amount of the antibody.

19. The method of claim 18, wherein PIK3CA has the amino acid sequence set forth in SEQ ID NO: 1.

20. The method of claim 19, wherein the one or more mutations in PIK3CA are selected from the group consisting of: E542K, E545K, E545G, E545D, Q546K, Q546R, M1043I, M1043V, H1047R, H1047L, H1047Y, G1049R and G1049S.

21. The method of claim 18, wherein the biological sample is assayed for PIK3CA mutations by analyzing nucleic acid obtained from the sample.

22. The method of claim 18, wherein the biological sample is assayed for PIK3CA mutations by analyzing proteins obtained from the sample.

23. The method of claim 18, wherein the cancer is breast cancer.

24. The method of claim 18, wherein the antibody is a monoclonal antibody.

25. The method of claim 18, wherein the biological sample is a tumor biopsy.

26. The method of claim 18, wherein the biological sample is an aspirate.

* * * * *

SEQUENCE LISTING

<160> NUMBER OF SEQ ID NOS: 2

<210> SEQ ID NO 1
<211> LENGTH: 1068
<212> TYPE: PRT
<213> ORGANISM: Artificial
<220> FEATURE:
<223> OTHER INFORMATION: Synthesized: Human PIK3CA -continued

<400> SEQUENCE: 1

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Met Asp Cys Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

```
Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
            435                 440                 445

Pro His Gly Leu Glu Asp Leu Leu Asn Pro Ile Gly Val Thr Gly Ser
            450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                    485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
            515                 520                 525

Glu Gln Leu Lys Ala Ile Ser Thr Arg Asp Pro Leu Ser Glu Ile Thr
            530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
            565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
            595                 600                 605

Pro Met Val Arg Gly Phe Ala Val Arg Cys Leu Glu Lys Tyr Leu Thr
            610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                    645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
            675                 680                 685

Glu Ser Tyr Cys Arg Ala Cys Gly Met Tyr Leu Lys His Leu Asn Arg
            690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                    725                 730                 735

Glu Gln Met Arg Arg Pro Asp Phe Met Asp Ala Leu Gln Gly Phe Leu
            740                 745                 750

Ser Pro Leu Asn Pro Ala His Gln Leu Gly Asn Leu Arg Leu Glu Glu
            755                 760                 765

Cys Arg Ile Met Ser Ser Ala Lys Arg Pro Leu Trp Leu Asn Trp Glu
            770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                    805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
            835                 840                 845
```

```
Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn  Leu Phe Ser Met Met  Leu Gly Ser
        995                 1000                1005

Gly Met  Pro Glu Leu Gln Ser  Phe Asp Asp Ile Ala  Tyr Ile Arg
    1010                1015                1020

Lys Thr  Leu Ala Leu Asp Lys  Thr Glu Gln Glu Ala  Leu Glu Tyr
    1025                1030                1035

Phe Met  Lys Gln Met Asn Asp  Ala His His Gly Gly  Trp Thr Thr
    1040                1045                1050

Lys Met  Asp Trp Ile Phe His  Thr Ile Lys Gln His  Ala Leu Asn
    1055                1060                1065

<210> SEQ ID NO 2
<211> LENGTH: 1367
<212> TYPE: PRT
<213> ORGANISM: Artificial
<220> FEATURE:
<223> OTHER INFORMATION: Synthesized: Human IGF1R

<400> SEQUENCE: 2

Met Lys Ser Gly Ser Gly Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140
```

```
Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

Glu Ser Ser Asp Ser Glu Gly Phe Val Ile His Asp Gly Glu Cys Met
290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
        355                 360                 365

Asn Ile Ala Ser Glu Leu Glu Asn Phe Met Gly Leu Ile Glu Val Val
    370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
        435                 440                 445

Ala Phe Asn Pro Lys Leu Cys Val Ser Glu Ile Tyr Arg Met Glu Glu
    450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                485                 490                 495

Ser Thr Thr Thr Ser Lys Asn Arg Ile Ile Ile Thr Trp His Arg Tyr
            500                 505                 510

Arg Pro Pro Asp Tyr Arg Asp Leu Ile Ser Phe Thr Val Tyr Tyr Lys
        515                 520                 525

Glu Ala Pro Phe Lys Asn Val Thr Glu Tyr Asp Gly Gln Asp Ala Cys
    530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
                565                 570                 575
```

-continued

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
            595                 600                 605

Ser Val Pro Ser Ile Pro Leu Asp Val Leu Ser Ala Ser Asn Ser Ser
610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
            645                 650                 655

Leu Tyr Arg His Asn Tyr Cys Ser Lys Asp Lys Ile Pro Ile Arg Lys
            660                 665                 670

Tyr Ala Asp Gly Thr Ile Asp Ile Glu Val Thr Gly Asn Pro Lys
            675                 680                 685

Thr Glu Val Cys Gly Gly Glu Lys Gly Pro Cys Cys Ala Cys Pro Lys
            690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
            725                 730                 735

Arg Lys Arg Arg Asp Val Met Gln Val Ala Asn Thr Thr Met Ser Ser
            740                 745                 750

Arg Ser Arg Asn Thr Thr Ala Ala Asp Thr Tyr Asn Ile Thr Asp Pro
            755                 760                 765

Glu Glu Leu Glu Thr Glu Tyr Pro Phe Phe Glu Ser Arg Val Asp Asn
            770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
            805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
            835                 840                 845

Phe Leu Lys Trp Pro Glu Pro Glu Asn Pro Asn Gly Leu Ile Leu Met
            850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
            885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
            915                 920                 925

Gly Tyr Glu Asn Phe Ile His Leu Ile Ile Ala Leu Pro Val Ala Val
            930                 935                 940

Leu Leu Ile Val Gly Gly Leu Val Ile Met Leu Tyr Val Phe His Arg
945                 950                 955                 960

Lys Arg Asn Asn Ser Arg Leu Gly Asn Gly Val Leu Tyr Ala Ser Val
            965                 970                 975

Asn Pro Glu Tyr Phe Ser Ala Ala Asp Val Tyr Val Pro Asp Glu Trp
            980                 985                 990

Glu Val Ala Arg Glu Lys Ile Thr  Met Ser Arg Glu Leu  Gly Gln Gly

-continued

```
                  995             1000            1005
Ser Phe Gly Met Val Tyr Glu Gly Val Ala Lys Gly Val Val Lys
    1010            1015            1020

Asp Glu Pro Glu Thr Arg Val Ala Ile Lys Thr Val Asn Glu Ala
    1025            1030            1035

Ala Ser Met Arg Glu Arg Ile Glu Phe Leu Asn Glu Ala Ser Val
    1040            1045            1050

Met Lys Glu Phe Asn Cys His His Val Val Arg Leu Leu Gly Val
    1055            1060            1065

Val Ser Gln Gly Gln Pro Thr Leu Val Ile Met Glu Leu Met Thr
    1070            1075            1080

Arg Gly Asp Leu Lys Ser Tyr Leu Arg Ser Leu Arg Pro Glu Met
    1085            1090            1095

Glu Asn Asn Pro Val Leu Ala Pro Pro Ser Leu Ser Lys Met Ile
    1100            1105            1110

Gln Met Ala Gly Glu Ile Ala Asp Gly Met Ala Tyr Leu Asn Ala
    1115            1120            1125

Asn Lys Phe Val His Arg Asp Leu Ala Ala Arg Asn Cys Met Val
    1130            1135            1140

Ala Glu Asp Phe Thr Val Lys Ile Gly Asp Phe Gly Met Thr Arg
    1145            1150            1155

Asp Ile Tyr Glu Thr Asp Tyr Tyr Arg Lys Gly Gly Lys Gly Leu
    1160            1165            1170

Leu Pro Val Arg Trp Met Ser Pro Glu Ser Leu Lys Asp Gly Val
    1175            1180            1185

Phe Thr Thr Tyr Ser Asp Val Trp Ser Phe Gly Val Val Leu Trp
    1190            1195            1200

Glu Ile Ala Thr Leu Ala Glu Gln Pro Tyr Gln Gly Leu Ser Asn
    1205            1210            1215

Glu Gln Val Leu Arg Phe Val Met Glu Gly Gly Leu Leu Asp Lys
    1220            1225            1230

Pro Asp Asn Cys Pro Asp Met Leu Phe Glu Leu Met Arg Met Cys
    1235            1240            1245

Trp Gln Tyr Asn Pro Lys Met Arg Pro Ser Phe Leu Glu Ile Ile
    1250            1255            1260

Ser Ser Ile Lys Glu Glu Met Glu Pro Gly Phe Arg Glu Val Ser
    1265            1270            1275

Phe Tyr Tyr Ser Glu Glu Asn Lys Leu Pro Glu Pro Glu Glu Leu
    1280            1285            1290

Asp Leu Glu Pro Glu Asn Met Glu Ser Val Pro Leu Asp Pro Ser
    1295            1300            1305

Ala Ser Ser Ser Ser Leu Pro Leu Pro Asp Arg His Ser Gly His
    1310            1315            1320

Lys Ala Glu Asn Gly Pro Gly Pro Gly Val Leu Val Leu Arg Ala
    1325            1330            1335

Ser Phe Asp Glu Arg Gln Pro Tyr Ala His Met Asn Gly Gly Arg
    1340            1345            1350

Lys Asn Glu Arg Ala Leu Pro Leu Pro Gln Ser Ser Thr Cys
    1355            1360            1365
```